United States Patent

Metzker et al.

[11] Patent Number: 5,994,063
[45] Date of Patent: Nov. 30, 1999

[54] SUBSTITUTED 4,4-DIFLUORO-4-BORA-3A, 4A-DIAZA-S-INDACENE COMPOUNDS FOR HOMOGENOUS AMPLIFICATION/ DETECTION ASSAYS

[76] Inventors: Michael L. Metzker, 7171 Buffalo Speedway #1621; Richard A. Gibbs, 3602 Gramercy, both of Houston, Tex. 77025

[21] Appl. No.: 08/612,036

[22] Filed: Mar. 7, 1996

Related U.S. Application Data

[63] Continuation-in-part of application No. 08/494,216, Jun. 23, 1995, Pat. No. 5,614,386.
[51] Int. Cl.$^6$ ...................................................... C12Q 1/68
[52] U.S. Cl. .............................. 435/6; 536/24.3; 536/26.6
[58] Field of Search .................................. 435/6, 5, 91.1, 435/91.2; 536/24.3–24.33, 26.6

[56] References Cited

U.S. PATENT DOCUMENTS

| | | | |
|---|---|---|---|
| 5,210,015 | 5/1993 | Gelfand et al. | 435/6 |
| 5,274,113 | 12/1993 | Kang et al. | 548/405 |
| 5,326,692 | 7/1994 | Brinkley et al. | 435/6 |
| 5,491,063 | 2/1996 | Fisher et al. | 435/6 |
| 5,538,848 | 7/1996 | Livak et al. | 435/6 |

FOREIGN PATENT DOCUMENTS

| | | |
|---|---|---|
| 9521266 | 8/1995 | WIPO . |

OTHER PUBLICATIONS

Holland et al., Detection of Polymerase Chain Reaction . . . PNAS, 88:7276–80 (1991).
Lee et al., Allelic discrimination by nick–translation PCR with fluorogenic probes, Nucleic Acid Res. 21:3761–66 (1993).

*Primary Examiner*—Scott W. Houtteman
*Attorney, Agent, or Firm*—Fulbright & Jaworski,L.L.P.

[57] ABSTRACT

The use of BODIPY® fluorophores for detecting a target nucleic acid is described. The parent heterocyclic molecule of the BODIPY® fluorophores is a dipyrrometheneboron difluoride compound which is modified to create a broad class of spectrally-discriminating fluorophores. The present invention provides oligonucleotides labelled with substituted 4,4-difluoro-4-bora-3A,4A-diaza-s-indacene (BODIPY® fluorophore) compounds for performing the Taqman assay.

14 Claims, 2 Drawing Sheets

5,994,063

SUBSTITUTED 4,4-DIFLUORO-4-BORA-3A, 4A-DIAZA-S-INDACENE COMPOUNDS FOR HOMOGENOUS AMPLIFICATION/DETECTION ASSAYS

This application is a continuation-in-part of U.S. Ser. No. 08/494,216 filed Jun. 23, 1995 now U.S. Pat. No. 5,614,386.

This invention was supported in part by a grant from the United States Government through the National Institutes of Health (Grant Nos. P30HG00210 (NIH) and T32HG00003 (NIH-NCHGR). The U.S. Government has certain rights in this invention.

FIELD OF THE INVENTION

The present invention provides oligonucleotides labelled with substituted 4,4-difluoro-4-bora-3A,4A-diaza-s-indacene (BODIPY® fluorophore) compounds for performing the Taqman assay.

BACKGROUND

The present invention provides oligonucleotides labelled with substituted 4,4-difluoro-4-bora-3A,4A-diaza-s-indacene (BODIPY® fluorophore) compounds for performing the Taqman assay. The ability to detect DNA and specific sequences of DNA is critical for understanding the function and control of genes and for diagnosis of genetically-inherited diseases. Native DNA consists of two linear polymers or strands of nucleotides. Each strand of DNA is a chain of nucleotides linked by phosphodiester bonds. The two strands are held together in an antiparallel orientation by hydrogen bonds between complementary bases of the nucleotides of the two strands: deoxyadenosine (A) pairs with thymidine (T) and deoxyguanosine (G) pairs with deoxycytidine (C).

A significant advance in DNA manipulation was the development of the polymerase chain reaction (PCR) technique as disclosed in U.S. Pat. Nos. 4,683,195; 4,683,195; and 4,800,159. The term "polymerase chain reaction" or "PCR" refers generally to the procedure involving: (1) treating extracted DNA to form single-stranded complementary strands; (2) adding a pair of oligonucleotide primers, wherein one primer of the pair is substantially complementary to part of the sequence in the sense strand and the other primer of each pair is substantially complementary to a different part of the same sequence in the complementary antisense strand; (3) annealing the paired primers to the complementary sequence; (4) simultaneously extending the annealed primers from a 3' terminus of each primer to synthesize an extension product complementary to the strands annealed to each primer wherein said extension products after separation from the complement serve as templates for the synthesis of an extension product for the other primer of each pair; (5) separating said extension products from said templates to produce single-stranded molecules; and (6) amplifying said single-stranded molecules by repeating at least once said annealing, extending and separating steps.

Detection methods generally employed in standard PCR techniques use a labeled probe with the amplified DNA in a hybridization assay. Other assays include the use of fragment length polymorphism (PCR FLP), hybridization to allele-specific oligonucleotide (ASO) probes (Saiki et al., Nature 324:163 (1986)), or direct sequencing via the dideoxy method (using amplified DNA rather than cloned DNA). The standard PCR technique operates by replicating a DNA sequence positioned between two primers, providing as the major product of the reaction a DNA sequence of discrete length terminating with the primer at the 5' end of each strand. Thus, insertions and deletions between the primers result in product sequence of different lengths, which can be detected by sizing the product in PCR-FLP. In an example of ASO hybridization, the amplified DNA is fixed to a nylon filter (by, for example UV irradiation) in a series of "dot blots", then allowed to hybridize with an oligonucleotide probe labeled with HRP under stringent conditions. After washing, tetramethylbenzidine (TMB) and hydrogen peroxide are added: HRP oxidizes the hydrogen peroxide, which in turn oxidizes the TMB to a blue precipitate, indicating hybridized probe.

While the PCR technique as presently practiced is an extremely powerful method for amplifying nucleic acid sequences, the detection of the amplified material requires additional manipulation and subsequent handling of the PCR products to determine whether the target DNA is present. It is desirable to decrease the number of subsequent handling steps required currently for the detection of amplified material.

Holland, et al., PNAS 88:7276–7280 (1991) describe an assay known as a Taqman assay. The 5'→3' exonuclease activity of Taq polymerase is employed in a polymerase chain reaction product detection system to generate a specific detectable signal concomitantly with amplification. An oligonucleotide probe, nonextendable at the 3' end, labeled at the 5' end, and designed to hybridize within the target sequence, is introduced into the polymerase chain reaction assay. Annealing of the probe to one of the polymerase chain reaction product strands during the course of amplification generates a substrate suitable for exonuclease activity. During amplification, the 5'→3' exonuclease activity of Taq polymerase degrades the probe into smaller fragments that can be differentiated from undegraded probe. The assay is sensitive and specific and is a significant improvement over more cumbersome detection methods. A version of this assay is also described in Gelfand et al., in U.S. Pat. No. 5,210,015. U.S. Pat. No. 5,210,015 to Gelfand, et al., and Holland, et al., PNAS 88:7276–7280 (1991) are hereby incorporated by reference.

Further, U.S. Pat. No. 5,491,063 to Fisher, et al., provides a Taqman-type assay. The method of Fisher et al. provides a reaction that results in the cleavage of single-stranded oligonucleotide probes labeled with a light-emitting label wherein the reaction is carried out in the presence of a DNA binding compound that interacts with the label to modify the light emission of the label. The method utilizes the change in light emission of the labeled probe that results from degradation of the probe. The methods are applicable in general to assays that utilize a reaction that results in cleavage of oligonucleotide probes, and in particular, to homogeneous amplification/detection assays where hybridized probe is cleaved concomitant with primer extension. A homogeneous amplification/detection assay is provided which allows the simultaneous detection of the accumulation of amplified target and the sequence-specific detection of the target sequence. U.S. Pat. No. 5,491,063 to Fisher, et al. is hereby incorporated by reference.

Lee, et al., NAR 21:3761–3766 (1993) describe nick translation PCR using fluorogenic probes. In this assay, two probes were used to detect mutant and wildtype cystic fibrosis alleles. Lee, et al., NAR 21:3761–3766 (1993) is incorporated herein by reference.

The present invention is drawn to provides oligonucleotides labelled with substituted 4,4-difluoro-4-bora-3A,4A- diaza-s-indacene (BODIPY® fluorophore) compounds for performing the Taqman assay.

SUMMARY OF THE INVENTION

BODIPY® fluorophores have improved spectral characteristics compared to conventional fluorescein and rhodamine dyes. The BODIPY® fluorophores have narrower band width, insensitivity to solvent or pH, and improved photostability. I is an object of the present invention to provide substituted 4,4-difluoro-4-bora-3A,4A-diaza-s-indacene (BODIPY® fluorophore)-labeled oligonucleotides for use in the Taqman assay.

Figure 1:
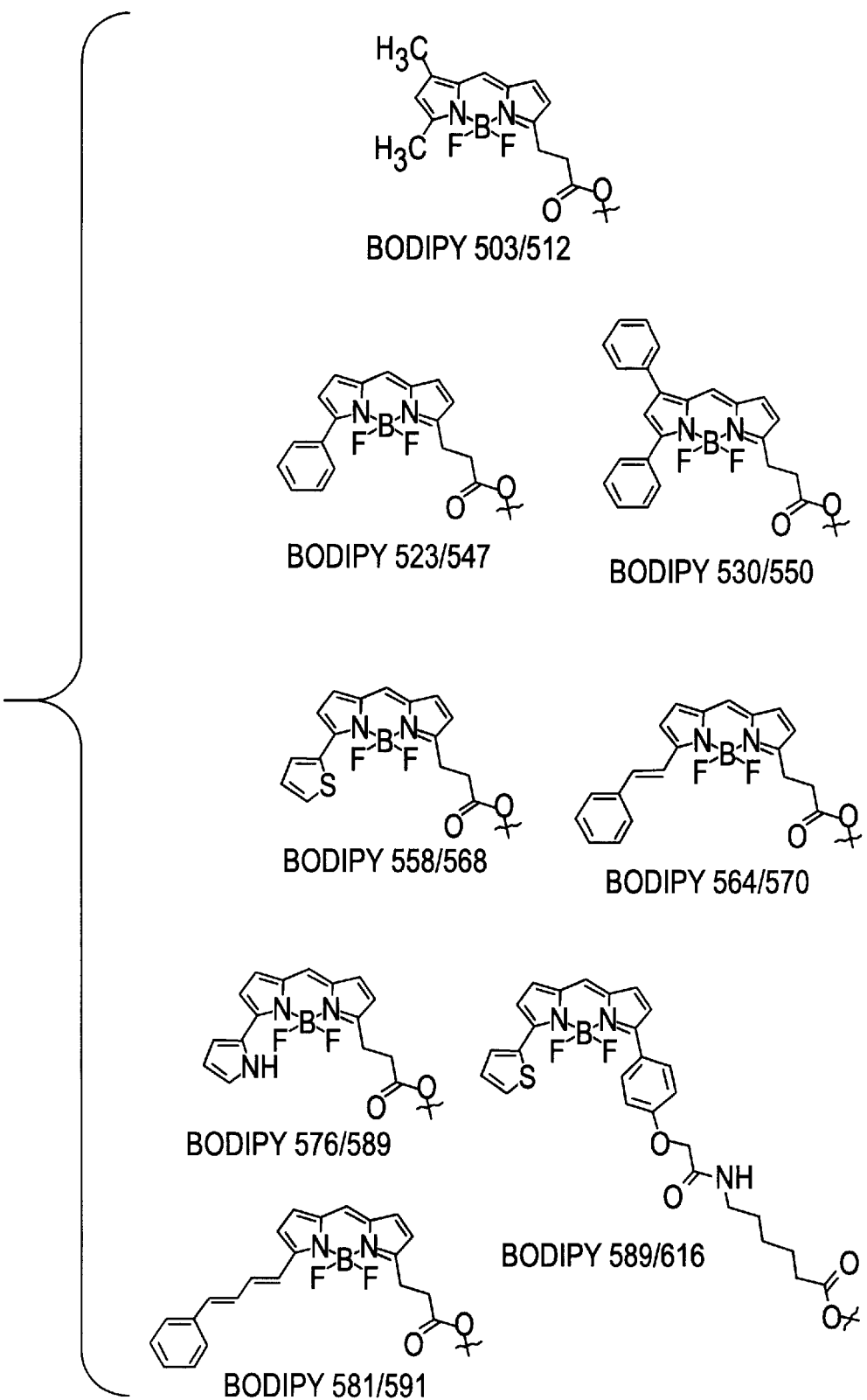
FIG. 1: Chemical structures of several substituted 4,4-difluoro-4-bora-3A,4A-diaza-s-indacene (BODIPY®) fluorophores are shown.
Figure 2A:
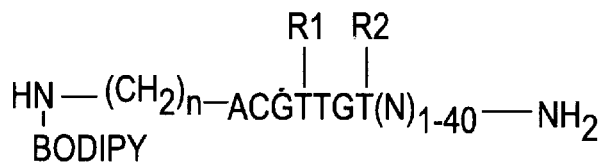
FIG. 2: (A) Double dye-labeled primers. Since different protecting groups block the linker arm amines, BODIPY energy transfer (BET) primers were first labeled internally with BODIPY 503/512, BODIPY 523/547 or BODIPY 530/550. After removal of the monomethoxytrityl group, BET primers were end-labeled with the BODIPY dye set. For BODIPY 503/512, BODIPY 523/547 or BODIPY 530/550 dyes, n=6, R1=$CH_3$, and R2=$(CH_2)_6$NHBODIPY. For BODIPY 558/568, BODIPY 564/570, BODIPY 576/589, BODIPY 581/591, and BODIPY 589/616 dyes, n=3, R1=$(CH_2)_6$NHBODIPY and R2=$CH_3$. Primers are blocked at the 3' end with a modified amino group ($NH_2$) to prevent polymerase extension of the probe. (B) Diagnostic application in determining reverse transcriptase resistance to antiviral drug therapy in patients infected with human immunodeficiency virus type-1 (HIV-1). Drug resistant markers have been previously described by B. A. Larder, "Reverse Transcriptase", A. M. Skalka and S. P. Goff, Eds., pp. 205–222 (Cold Spring Harbor Laboratory Press, 1993). BET probe labeled with BODIPY 503/512 is specific for the wild-type sequence and BET probe labeled with BODIPY 523/547 is specific for the drug resistance sequence.
Figure 2B:
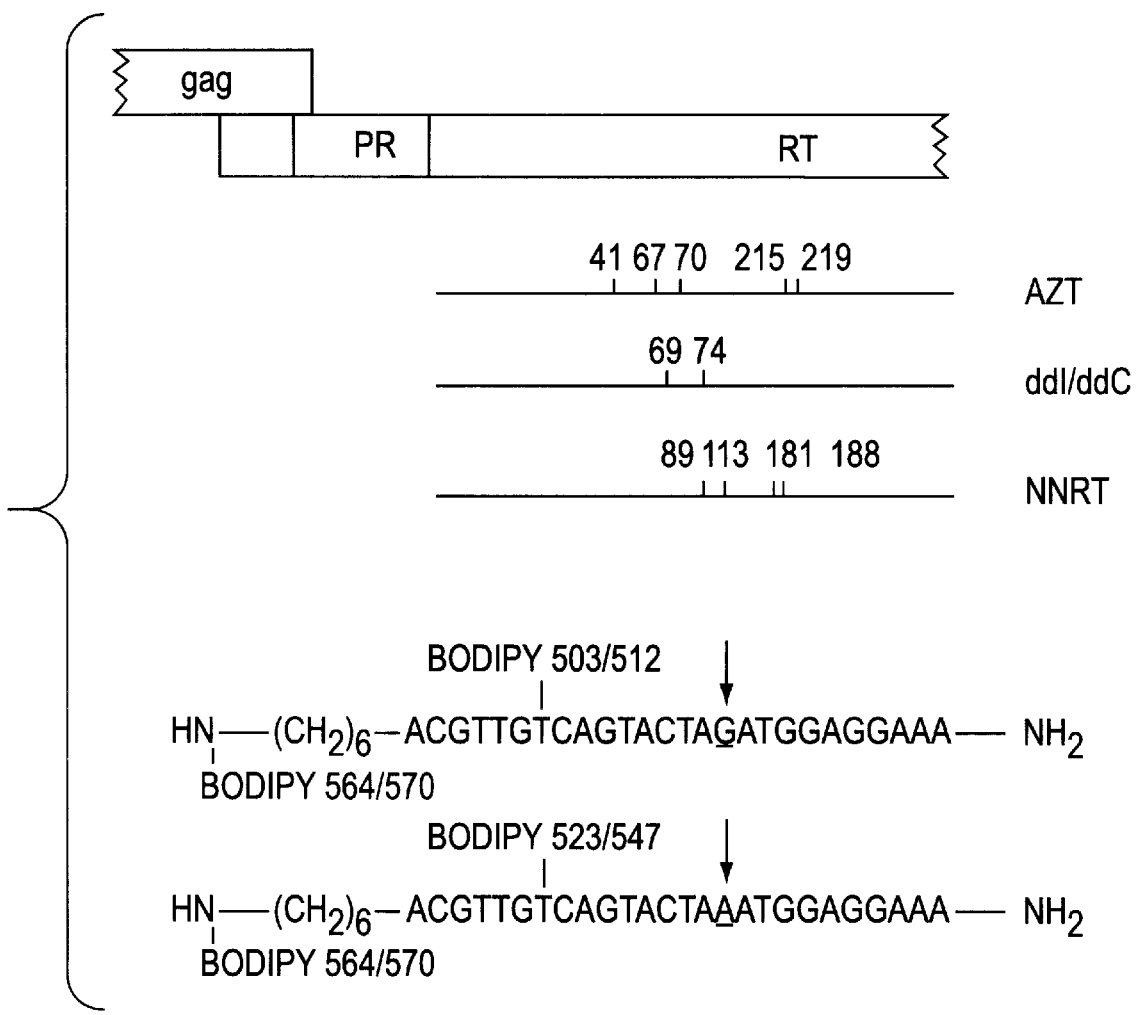

The drawings and figures are not to scale and certain features mentioned may be exaggerated in scale or shown in schematic form in the interest of clarity and conciseness.

DETAILED DESCRIPTION OF THE INVENTION

It will be apparent to one skilled in the art that various substitutions and modifications may be made to the invention disclosed herein without departing from the scope and the spirit of the invention.

As used herein, "BODIPY®" shall refer to a broad class of modified, spectrally-discriminating fluorophores wherein the parent heterocyclic molecule is a dipyrromethenboron difluoride compound. Specific BODIPY® fluorophores useful in the present invention include BODIPY®s with adsorption maxima of about 450 to 700, and emission maxima of about 450 to 700. Preferred embodiments include BODIPY®s with adsorption maxima of about 480 to 650, and emission maxima of about 480 to 650. Examples of preferred embodiment BODIPY®s include BODIPY® 503/512-SE (4,4-difluoro-5,7-dimethyl-4-bora-3a,4a-diaza-s-indacene-3-propionicacid), BODIPY®523/547 (4,4-difluoro-5-phenyl-4-bora-3a,4a-diaza-s-indacene-3-propionic acid), BODIPY® 564/570 (4,4-difluoro-5-styryl-4-bora-3a,4a-diaza-s-indacene-3-propionicacid),BODIPY® 576/589 (4,4-difluoro-5-(2-pyrrolyl)-4-bora-3a,4a-diaza-s-indacene-3-propionic acid), BODIPY® 581/591 (4,4-difluoro-5-(4-phenyl-1,3-butadienyl)-4-bora-3a,4a-diaza-s-indacene-3-propionic acid).

As used herein, "Taqman" or "Taqman assay" refers to assays that utilize the 5'→3' exonuclease activity of Taq polymerase in a polymerase chain reaction to generate a specific detectable signal concomitantly with amplification. An oligonucleotide probe, nonextendable at the 3' end, labeled at the 5' end, and designed to hybridize within the target sequence, is introduced into the polymerase chain reaction assay. Annealing of the probe to one of the polymerase chain reaction product strands during the course of amplification generates a substrate suitable for exonuclease activity. During amplification, the 5'→3' exonuclease activity of Taq polymerase degrades the probe into smaller fragments that can be differentiated from undegraded probe. The assay is sensitive and specific and is a significant improvement over more cumbersome detection methods. In one such assay, the oligonucleotide that is degraded has at least two light-emitting fluorophores attached. The fluorophores interact each other to modify (quench) the light emission of the fluorophores. The 5'-most fluorophore is the quencher fluorophore. The 3'-most fluorophore is the quenched fluorophore. In another type of Taqman assay, an oligonucleotide probe is labeled with a light-emitting quenched fluorophore wherein the reaction is carried out in the presence of a DNA binding compound (quenching agent) that interacts with the fluorophore to modify the light emission of the label.

As used herein, "labeled oligonucleotide" refers to the oligonucleotide in the Taqman assay that is labeled with at least two BODIPY® fluorophores.

As used herein, "quenched" refers to the interaction of the at least two BODIPY® fluorophores on the labeled oligonucleotide wherein when both BODIPY® fluorophores are present on the labeled oligonucleotide, fluorescence of either fluorophore is not detected.

As used herein, "quencher fluorophore" refers to the BODIPY® fluorophore at a position most 5' on the labeled oligonucleotide.

As used herein, "quenched fluorophore" refers to the BODIPY® fluorophore at a position most 3' on the labeled oligonucleotide.

As used herein, "quencher agent" refers to intercalating compounds and the like similar to ethidium bromide for use in a Taqman assay similar to that used in the method of Fisher, et al., U.S. Pat. No. 5,491,063.

As used herein, "5' position" refers to the 5' position on the deoxyribose moiety of a polynucleotide.

As used herein, "3' position" refers to the 3' position on the deoxyribose moiety of a nucleotide.

One novel aspect of the present invention is to provide an oligonucleotide substituted with at least two 4,4-difluoro-4-bora-3A,4A-diaza-s-indacene (BODIPY®) fluorophores for performing a Taqman assay, wherein a first 4,4-difluoro-4-bora-3A,4A-diaza-s-indacene (BODIPY®) fluorophore is a quencher fluorophore and a second 4,4-difluoro-4-bora-3A, 4A-diaza-s-indacene (BODIPY®) fluorophore is a quenched fluorophore.

A preferred embodiment of the present invention provides BODIPY® 564/570 (4,4-difluoro-5-styryl-4-bora-3a,4a-diaza-s-indacene-3-propionic acid) as a quencher fluorophore.

An additional preferred embodiment of the present invention provides BODIPY® 576/589 (4,4-difluoro-5-(2- pyrrolyl)-4-bora-3a,4a-diaza-s-indacene-3-propionic acid) as a quencher fluorophore.

A further preferred embodiment of the present invention provides BODIPY® 581/591 (4,4-difluoro-5-(4-phenyl-1,3-butadienyl)-4-bora-3a,4a-diaza-s-indacene-3-propionic acid) as a quencher fluorophore.

Another preferred embodiment of the present invention provides BODIPY® 558/568 (4,4-difluoro-5-(2-thienyl)-4bora-3a,4a-diaza-s-indacene-3-propionic acid) as a quencher fluorophore.

Yet a further preferred embodiment of the present invention provides BODIPY® 581/591 (4,4-difluoro-5-(4-phenyl-1,3-butadienyl)-4-bora-3a,4a-diaza-s-indacene-3-propionic acid) as a quencher fluorophore.

An additional preferred embodiment of the present invention provides BODIPY® 503/512-SE(4,4-difluoro-5,7-dimethyl-4-bora-3a,4a-diaza-s-indacene-3-propionicacid) as a quenched fluorophore.

Yet another preferred embodiment of the present invention provides BODIPY® 523/547 (4,4-difluoro-5-phenyl-4-bora-3a,4a-diaza-s-indacene-3-propionic acid) as a quenched fluorophore.

Another preferred embodiment of the present invention provides BODIPY° 530/550 (4,4-difluoro-5,7-diphenyl-4-bora-3a,4a-diaza-s-indacene-3-propionic acid) as a quenched fluorophore.

Another aspect of the present invention provides an oligonucleotide substituted with at least one 4,4-difluoro-4-bora-3A,4A-diaza-s-indacene (BODIPY®) fluorophores for performing a Taqman assay, wherein said at least one 4,4-difluoro-4-bora-3A,4A-diaza-s-indacene (BODIPY®) fluorophore is a quenched fluorophore and a quencher agent is present in said Taqman assay. Any of the quenched (BODIPY®) fluorophores mentioned above can be used.

The following examples are offered by way of illustration and are not included to limit the invention in any manner. The examples show the procedures for synthesizing BODIPY®-tagged primers and performing DNA sequencing with said primers.

EXAMPLE 1

A. Reagents:

DNA synthesis reagents were purchased from ABI except 5'-amino-modifier C3, C6, and C12 and amino modifier C6 dT phosphoramidites and 3'-amino-modifier CPG were purchased from Glen Research. Oligonucleotides BET primers were synthesized on 3'-amino-modifier CPG column trityl-on, auto-cleavage using either an BI model 380B or model 394 DNA synthesizer. All BODIPY-SE dyes were purchased from Molecular Probes. BODIPY-SE dye were resuspended in anhydrous DMSO (50 mg/mL).

B. Fluorescent primers:

The leader sequences for BET dye-primers are 5'-NTGTT* or 5'-NACGTTGT* followed by any primer sequence that is completely complementary to the target sequence. Primers were synthesized (0.2 μmole) using either C3 or C6 amino link (N) and C6dT (T*) and resuspended in 400 μl of 0.01 N NaOH. To each tube, 10 μl of BODIPY 503/512-SE, BODIPY 523/547 or BODIPY 530/550 was added, incubated at 25° C. for 10 min., ethanol precipitated, incubated in 200 μl of 80% acetic acid for 20 min., and ethanol precipitated. BODIPY primers were resuspended in 200 μL of 0.25 M NaHCO$_3$/Na$_2$CO$_3$, pH 9.0 buffer and 10 μL of either BODIPY 588/568-SE, BODIPY 564/570-SE, BODIPY 576/589-SE, BODIPY 581/591-SE, or BODIPY 589/616-SE, was added and the mixtures were incubated at 25° C. for 16 h. Following ethanol precipitation, dye-labeled primers were purified by RP-HPLC, resuspended in deionized (DI) water, and diluted to 0.4 pmol/μl.

C. RP-HPLC.

The RP-HPLC hardware system consisted of a Beckman model 127 gradient solvent module, a Rheodyne model 7125 injector, an Applied Biosystems (ABI) model 759A absorbance detector, and a Spectra-Physics model SP4600 DataJet integrator. Gradient RP-HPLC was performed using an ABI aquapore RP-300 column (4.6 mm×250 mm) where "Buffer A" is 100 mM triethylammonium acetate (TEAA), pH 7.0 and "Buffer B" is 100 mM TEAA 70% (v/v) acetonitrile. Dye-labeled oligonucleotides were purified using the following gradient conditions: 20% B, 5 minutes; 20% B-40% B, 30 minutes; 40% B- 100% B, 18 minutes; 100% B, 5 minutes at a flow rate of 1.0 ml per minute.

One skilled in the art will appreciate readily that the present invention is well adapted to carry out the objects and obtain the ends and advantages mentioned, as well as those inherent therein. The oligonucleotides, dyes, methods, procedures and techniques described herein are presently representative of the preferred embodiments, are intended to be exemplary, and are not intended as limitations on the scope of the invention. Changes therein and other uses will occur to those skilled in the art, and are encompassed within the spirit of the invention or defined by the scope of the appended claims. All references specifically cited herein are incorporated by reference.

We claim:

1. An oligonucleotide substituted with two 4,4-difluoro-4-bora-3A,4A-diaza-s-indacene (BODIPY®) fluorophores for performing a Taqman assay, wherein a first 5'-most 4,4-difluoro-4-bora-3A,4A-diaza-s-indacene (BODIPY®) fluorophore is a quencher fluorophore and a second 3'-most 4,4-difluoro-4-bora-3A,4A-diaza-s-indacene (BODIPY®) fluorophore is a quenched fluorophore.

2. The oligonucleotide of claim 1, wherein said quencher fluorophore is BODIPY® 564/570 (4,4-difluoro-5-styryl-4-bora-3a,4a-diaza-s-indacene-3-propionic acid).

3. The oligonucleotide of claim 1, wherein said quencher fluorophore is BODIPY®576/589(4,4-difluoro-5-(2-pyrrolyl)-4-bora-3a,4a-diaza-s-indacene-3-propionic acid).

4. The oligonucleotide of claim 1, wherein said quencher fluorophore is BODIPY® 581/591 (4,4-difluoro-5-(4-phenyl-1,3-butadienyl)-4-bora-3a,4a-diaza-s-indacene-3-propionic acid).

5. The oligonucleotide of claim 1, wherein said quenched fluorophore is BODIPY® 503/512-SE (4,4-difluoro-5,7-dimethyl-4-bora-3a,4a-diaza-s-indacene-3-propionic acid).

6. The oligonucleotide of claim 1, wherein said quenched fluorophore is BODIPY® 558/568 (4,4-difluoro-5-(2-thienyl)-4-bora-3a,4a-diaza-s-indacene-3-propionic acid).

7. The oligonucleotide of claim 1, wherein said quenched fluorophore is BODIPY® 589/616 (6-(((4-(4,4-difluoro-5-(2-thienyl)-4-bora-3a,4a-diaza-s-indacene-3-yl)phenoxy) acetyl)amino)hexanoic acid).

8. The oligonucleotide of claim 1, wherein said quenched fluorophore is BODIPY® 523/547 (4,4-difluoro-5-phenyl-4-bora-3a,4a-diaza-s-indacene-3-propionic acid).

9. The oligonucleotide of claim 1, wherein said quenched fluorophore is BODIPY® 530/550 (4,4-difluoro-5,7-diphenyl-4-bora-3a,4a-diaza-s-indacene-3-propionic acid).

10. A composition of matter comprising an oligonucleotide substituted with at least one 4,4-difluoro-4-bora-3A, 4A-diaza-s indacene (BODIPY®) fluorophore and an agent that interacts with the fluorophore to absorb the light emitted by the fluorophore.

11. The composition of claim 10, wherein said quenched fluorophore is BODIPY® 589/616 (6-(((4(4,4-difluoro-5-(2-thienyl)-4-bora-3a,4a-diaza-s-indacene-3-yl)phenoxy)acetyl)amino)hexanoic acid).

12. The composition of claim 10, wherein said quenched fluorophore is BODIPY® 523/547 (4,4difluoro-5-phenyl-4bora-3a,4a-diaza-s-indacene-3-propionic acid).

13. The composition of claim 10, wherein said quenched fluorophore is BODIPY®530/550 (4,4-difluoro-5,7-diphenyl-4-bora-3a,4a-diaza-s-indacene-3-propionic acid).

14. An oligonucleotide substituted with at least two different 4,4-difluoro-4-bora-3A,4A-diaza-s indacene (BODIPY®) fluorophores, each fluorophore being capable of absorbing and emitting light, the fluorophores attached to the oligonucleotide such that the light emitted by at least one fluorophore is absorbed by at least one different fluorophore.

* * * * *